(12) United States Patent
Chiou et al.

(10) Patent No.: US 7,941,201 B2
(45) Date of Patent: May 10, 2011

(54) MICROPROBE ARRAY STRUCTURE AND METHOD FOR MANUFACTURING THE SAME

(75) Inventors: Jin-Chern Chiou, Hsinchu (TW); Chen-Chun Hung, Linyuan Township, Kaohsiung County (TW); Chih-Wei Chang, Yangmei Township, Taoyuan County (TW)

(73) Assignee: National Chiao Tung University, Hsinchu (TW)

( * ) Notice: Subject to any disclaimer, the term of this patent is extended or adjusted under 35 U.S.C. 154(b) by 1198 days.

(21) Appl. No.: 11/599,303

(22) Filed: Nov. 15, 2006

(65) Prior Publication Data

US 2008/0009763 A1 Jan. 10, 2008

(30) Foreign Application Priority Data

Jun. 9, 2006 (TW) .............................. 95120528 A

(51) Int. Cl.
*A61B 5/04* (2006.01)
(52) U.S. Cl. ........................ 600/373; 600/393
(58) Field of Classification Search .................. 600/373, 600/393
See application file for complete search history.

(56) References Cited

U.S. PATENT DOCUMENTS

| | | | |
|---|---|---|---|
| 6,091,975 A * | 7/2000 | Daddona et al. .............. 600/345 |
| 6,334,856 B1 | 1/2002 | Allen et al. |
| 6,622,035 B1 | 9/2003 | Merilainen et al. |
| 6,690,959 B2 | 2/2004 | Thompson |
| 6,782,283 B2 | 8/2004 | Schmidt et al. |
| 2002/0082543 A1* | 6/2002 | Park et al. ....................... 604/21 |
| 2004/0054393 A1 | 3/2004 | Stemme et al. |

OTHER PUBLICATIONS

P. Griss, P. Enoksson, H.K. Tolvanen-Laakso, P. Merilainen, S. Ollmar, G. Stemme, "Micromachined Electrodes for Biopotential Measurements", J. of Microelectromechanical System, vol. 10, No. 1, 2001.

* cited by examiner

*Primary Examiner* — Lee S Cohen
(74) *Attorney, Agent, or Firm* — Rosenberg, Klein & Lee

(57) ABSTRACT

A microprobe array structure with self-stabilization capability and a method for manufacturing the same are proposed. The microprobe array structure is used to sense various biopotential signals, and is characterized in that the etching parameters are controlled during etching to manufacture a microprobe structure with a reduced bottom cross section so that the microprobe can be firmly stabilized in the skin tissue. Moreover, a conducting layer is formed on the microprobe to sense signals. A design of electric isolation between microprobes is also proposed. The microprobe array can therefore be used for the measurement of various biopotential signals, and can also be used as a stimulus.

33 Claims, 21 Drawing Sheets

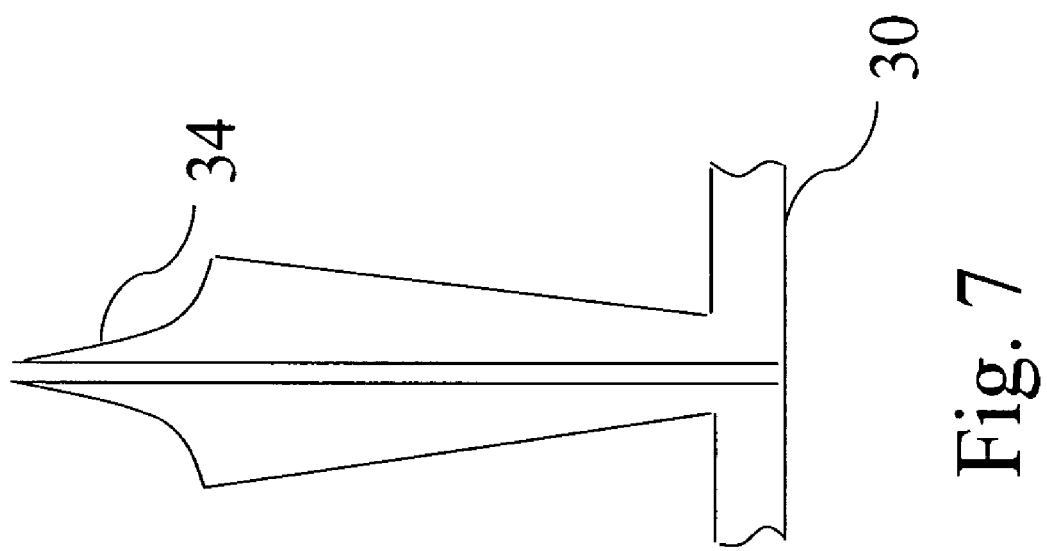

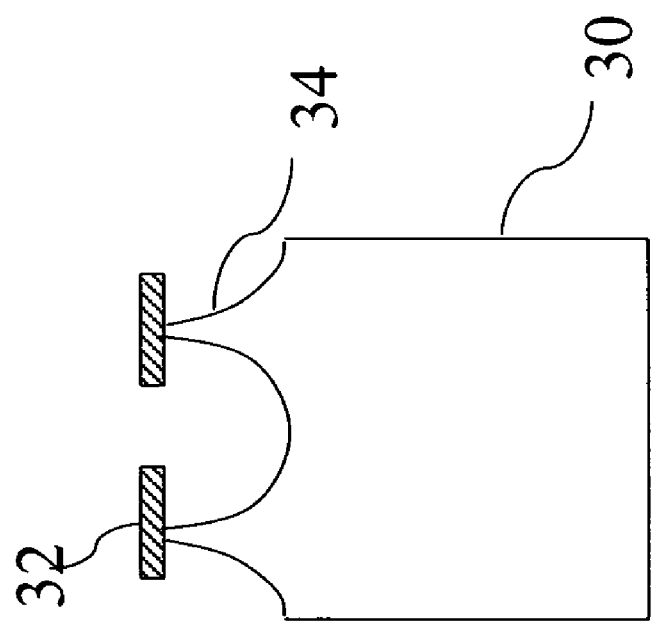

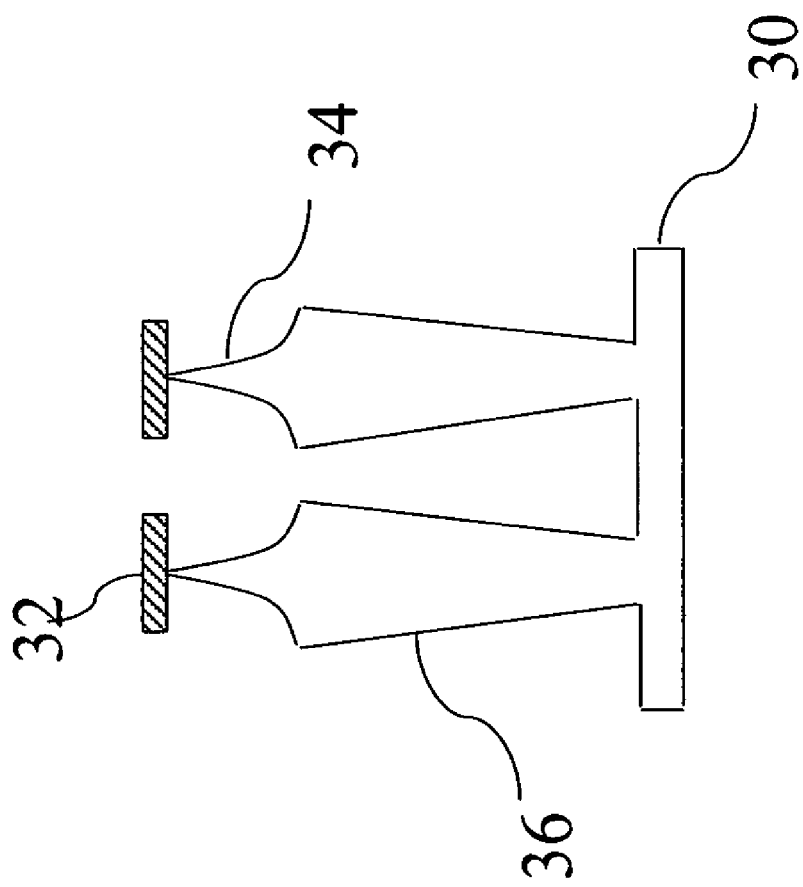

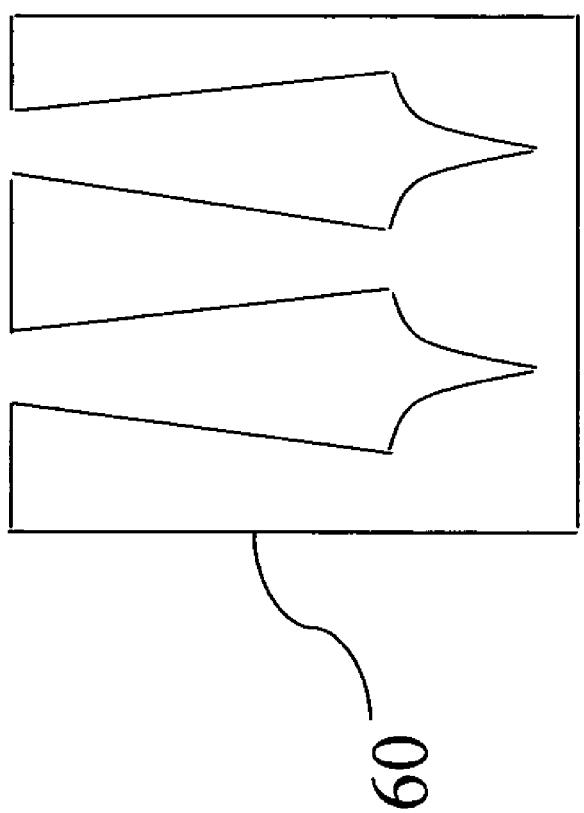

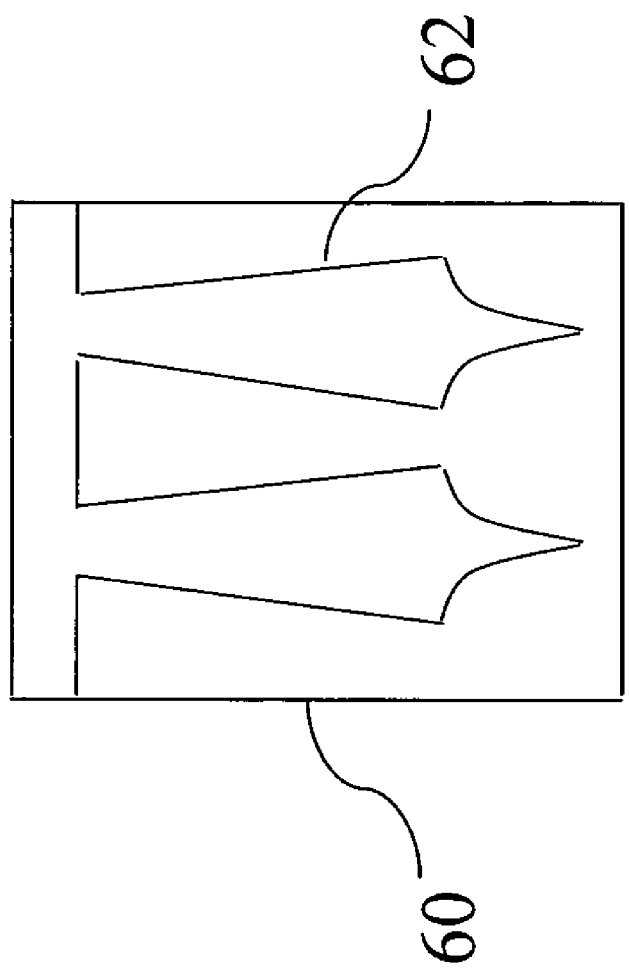

MICROPROBE ARRAY STRUCTURE AND METHOD FOR MANUFACTURING THE SAME

FIELD OF THE INVENTION

The present invention relates to a microprobe array structure and a method for manufacturing the same and, more particularly, to a microprobe array structure with self-stabilization capability for biopotential signals measurements, and a method for manufacturing the same.

BACKGROUND OF THE INVENTION

Electrodes for measuring biopotential are used extensively in modern clinical and biomedical applications. These applications encompass numerous physiological tests including electrocardiography (ECG/EKG), electroencephalography (EEG), electrical impedance tomography (EIT), electromyography (EMG) and electro-oculography (EOG). The electrodes for these types of physiological tests function as a transducer by transforming the electric potentials or biopotentials within the body into an electric voltage that can be measured by conventional measurement and recording devices.

Most physiological electrodes for such applications are placed on the skin. The skin presents a layered architecture. Generally, the outer skin layer, stratum corneum, forms the primary barrier of the body. It constantly is renewing itself and consists of dry, dead cells, which dramatically influences electrical isolation characteristics, i.e., creates high electrical impedance, compared to living cells. It also renders the administration of drugs on the skin less effective. Typically, the skin must be prepared prior to the application of electrodes or treatment.

Below the stratum corneum are several other layers, including the stratum germinativum. The stratum germinativum, is the area where the cells divide, grow, and are displaced outward to the stratum corneum. Since the stratum germinativum is composed of living cells that predominately consist of liquid, this layer of the skin is an electrically conducting tissue comparable to an electrolyte. The stratum corneum, further is very thin and uniform in most regions of the body surface ranging from 13-15 μm with a maximum of about 20 μm. The dermis, which is below the stratum germinativum, contains vascular and nervous components as well as sweat glands and hair follicles and is also electrically conducting. It is in the dermis that pain has its origins.

FIG. 1 shows the sensing electrode used in a conventional biopotential measurement system. In order to get over the high impedance of the Stratum Corneum 12 with bad electric conductivity, it is necessary to reduce or remove the Stratum Cornuem (including shaving of the area) or use electric conductive adhesive 18 or similar material under the sensing electrode 10 to moisten the Stratum Corneum 12 so as to enhance the conductive effect. The whole measuring effect, however, is much limited, due to drying, irritation, movement and other well documented problems. Similar or additional problems are associated with "dry" electrodes. Therefore, U.S. Pat. No. 6,334,856 discloses a microneedle device 20 shown in FIG. 2 as a sensing electrode, wherein the microneedle 22 penetrates the Stratum Corneum 12 and gets into the Stratum Germinativum 14 to measure biopotential signals. Because the Stratum Germinativum 14 consists of live cells and has a good electric conductivity, the microneedle device 20 requires no electric conductive adhesive to obtain better measuring results. Moreover, the length of the microneedle 22 can be controlled not to get into the dermis 16, hence not causing pain or bleeding to the human body. Because the microprobe has the above advantages, it has replaced the conventional sensing electrode and been widely used in the biopotential measurement systems.

When the microneedle device 20 is used as a sensing electrode, a certain external force is applied to let the microneedle 22 puncture the Stratum Corneum 12 and get into the Stratum Germinativum 14. Because the skin tissue will continually push outwards the microneedle 22 and the microneedle device 20 is of a conical shape that has a wide bottom and a narrow top and hence has no stabilization capability, the actions of the muscles under the skin will easily loosen the probe 22. Therefore, it is necessary to use a fixing tool such as adhesive tape to fix the microneedle device 20 on the skin. Since the skin tissue is very soft, the fixing effect of the microneedle device 20 varies, hence affecting the position where the probe 22 gets into the skin and making the quality of signal measurement hard to control. In consideration of this inherent problem, U.S. Pat. No. 6,690,959 discloses a microprobe structure having a probe with an inverted hooked pinpoint to let the microprobe "lodge" within the skin. But forming an inverted hook on a microprobe structure at the micrometer level is very difficult to manufacture utilizing current technique, which the patent did not disclose a feasible manufacturing method either. Although PCT Application No. WO 01/52731 discloses a process for deriving a more durable barbed spike, both probes suffer from potential breakage of the barb or damage to the skin due to probe movement caused by the barb.

Accordingly, the present invention aims to propose a microprobe array structure having a self-stabilization function and capable of measuring biopotential signals and a method for manufacturing the same.

SUMMARY OF THE INVENTION

To achieve these and other advantages and in order to overcome the disadvantages of the conventional method in accordance with the purposes of the invention as embodied and broadly described herein, the present invention provides a microprobe array structure with self-stabilization capability. The microprobe array structure can be used as a stimulus or a sensing electrode in biopotential measurement systems to measure various biopotential signals. Moreover, the drawback that the conventional microprobe array cannot be firmly stabilized in the skin tissue can be overcome.

Because the microprobe has the tip portion 34 and can puncture the Stratum Corneum 50 to get into the Stratum Germinativum 52, better electric conductivity can be obtained. Moreover, because the microprobe is self-stabilizing within the Stratum Germinativum, the biopotential measurements can be better made and/or maintained. Therefore, the microprobe won't easily loosen up in the skin tissue, and has a self-stabilization capability to overcome the drawback that the conventional microprobe array cannot be firmly stabilized in the skin tissue. Further, because the microprobe exploits the skins natural elastic/contractile property to self-stabilize; the microprobe does not anchor itself into tissue causing potential damage to the adjacent cells as with barbed spikes/probes.

Another object of the present invention is to provide a method for manufacturing a microprobe array structure. The method has a simple manufacturing process that can be easily carried out. Therefore, the manufactured microprobe array has a low cost and can be mass produced.

To achieve the above objects, the present invention provides a method for manufacturing a microprobe structure. One preferred method comprises the steps of: providing a substrate and forming a patterned masking layer thereon; isotropically etching a plurality of tip portions with the masking layer as the mask; anisotropically etching downwards a plurality of needles and controlling etching parameters to let the cross-sectional area of the connection between the needle and the tip portion be larger than that of the other end of the needle; removing the masking layer to get said microprobe structure; and forming a conducting layer on the microprobe structure. The microprobe array manufactured by the above method comprises a substrate and a plurality of microprobes. Each of the microprobes has a tip portion, a needle and a conducting layer. The top of the needle is connected to the tip portion. The bottom of the needle is connected to the substrate. The cross-sectional area of the top is larger than that of the bottom. The conducting layer covers on the tip portion and the needle. When the microprobe array is used as a sensing electrode used in the skin tissue, the substrate 30 can be connected to an external circuit to transmit the measured biopotential signals to the circuit.

BRIEF DESCRIPTION OF THE DRAWINGS

The various objects and advantages of the present invention will be more readily understood from the following detailed description when read in conjunction with the appended drawings, in which:

FIG. 7 is a diagram of a microprobe with hollow structure according to an embodiment of the present invention;

FIGS. 8(a) to 8(k) show the manufacturing steps of a microprobe array structure according to an embodiment of the present invention; and FIG. 9(a) to 9(c) show another manufacturing steps of a microprobe array structure according to an embodiment of the present invention.

DETAILED DESCRIPTION OF THE PREFERRED EMBODIMENTS

It is the object of the present invention to provide a self stabilizing electrode suitable for mounting on the skin of a patient and which provides an improved signal to noise ratio to the bioelectrical signal obtained by the electrode. The present invention proposes an improved microprobe structure with inherent self-stabilizing features which can be used to measure various biopotential signals as electrocardiography (ECG/EKG) signals, electroencephalography (EEG) signals, electrical impedance tomography (EIT) signals, electromyography (EMG) signals and electro-oculography (EOG) signals. As used herein, the terms "biopotential", "bioelectrical" and "biosignal" are used interchangeably and generally refer to the information received from the invention electrodes.

Figure 1:
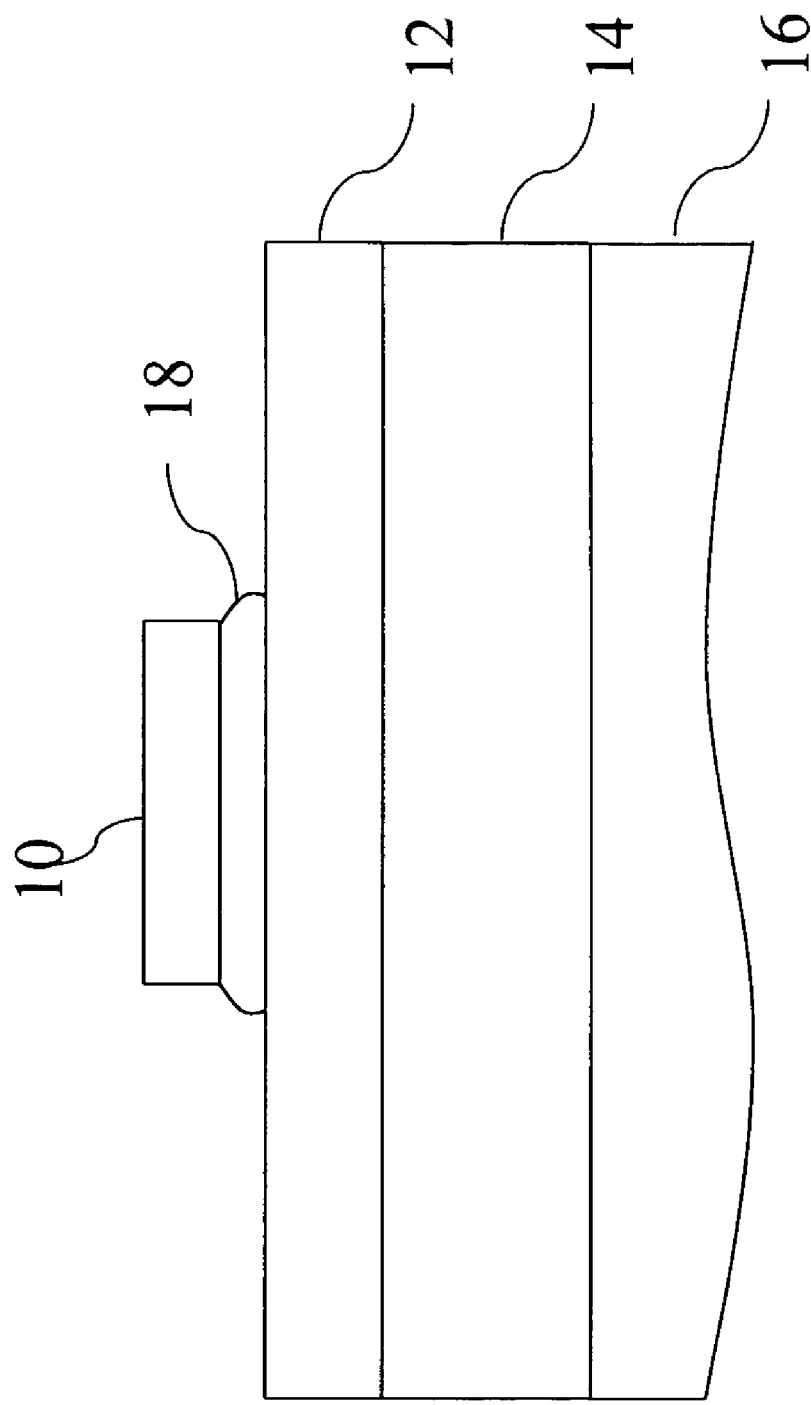
FIG. 1 is a diagram of a conventional sensing electrode for measuring biopotential signals.
Figure 2:
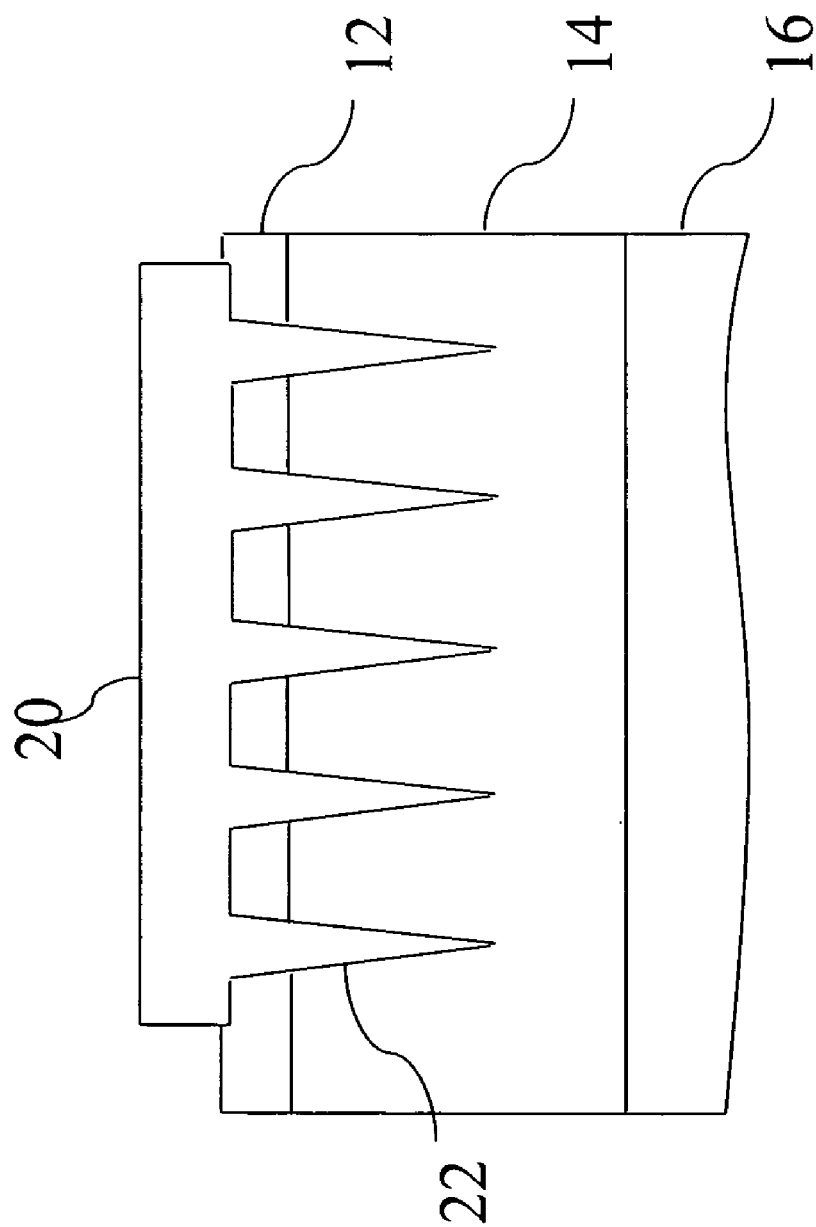
FIG. 2 is a diagram of a conventional microprobe array used as a sensing electrode for measuring biopotential signals.
Figure 3:
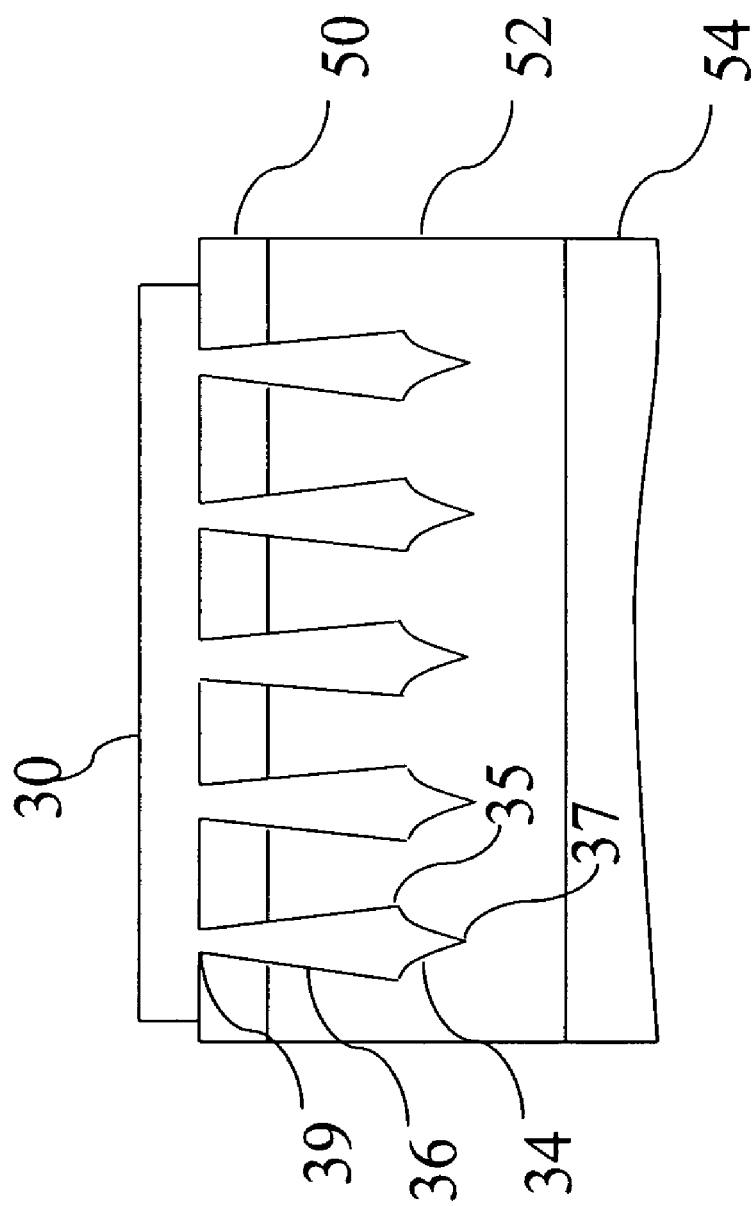
FIG. 3 is a diagram of a microprobe array of the present invention used as a sensing electrode for measuring biopotential signals

The microprobe electrode of the present invention reduces skin impedance and artifacts by increasing signal quality through use of microprobes to penetrate the Stratum Corneum into viable epidermis. In addition to the capability of puncturing the Stratum Corneum of the skin, the microprobe of the present invention has also the self-stabilization function in the skin tissue. Moreover, the micro-electro-mechanical manufacturing process is very stable and simple. In a preferred embodiment, as shown in FIG. 3, a microprobe array comprises a substrate 30. A plurality of microprobes is disposed on the substrate 30. Each microprobe has a tip portion 334, the bottom portion 36, and a conducting layer (not shown). The top of the needle 36 is connected to the tip portion 34, and the connection between the tip portion 34 and the bottom portion of the needle 36 has a neck 35 defined by an acute contour terminating at point 37. The base of the needle 39 is connected to the substrate 30. The cross-sectional view of the top of the needle shows the neck 35 is wider than that of the bottom of the needle 36. The conducting layer covers on the tip portion 34 and the needle 36.

In a preferred embodiment of the present invention, the microprobes tip needs to be sufficiently sharp and rigid to penetrate the skin of a patient. Although preferable, the tip portion 34, comprising the point 37 to the neck 35 of the microprobe, needs not necessarily to be of the circular or elliptical arc shape as shown in FIG. 3. The tip portion 34 can also be of the sharp angular shape shown in FIG. 4, or of the smooth shape shown in FIG. 5, or of a combination thereof, like the shape shown in FIG. 6. FIG. 7 illustrates that while the function of the microprobes may be preserved by the tip being sufficiently sharp and ending in a point, the microprobes can be made hollow to allow a drug to be passed through throughholes in substrate 30 into the microprobes responsive to pressure on the capsule, similar to many small injection needles, creating a transdermal patch/electrode. Hollow microprobes could also be employed to extract small amounts of fluids/extracts, preferably by capillary action, or small amounts of fluids could be flushed into the epidermis and could be reabsorbed for analysis of content. This could be readily employed for determination of compositional information such as glucose or other such information.

Figure 4:
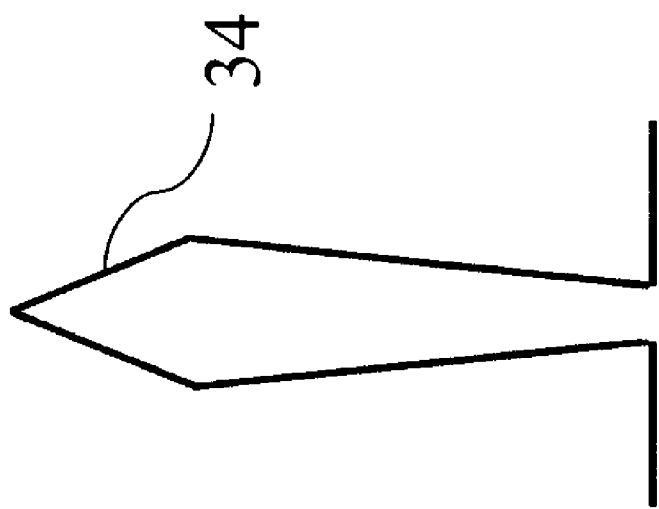
FIG. 4 is a diagram of a microprobe structure according to an embodiment of the present invention.
Figure 5:
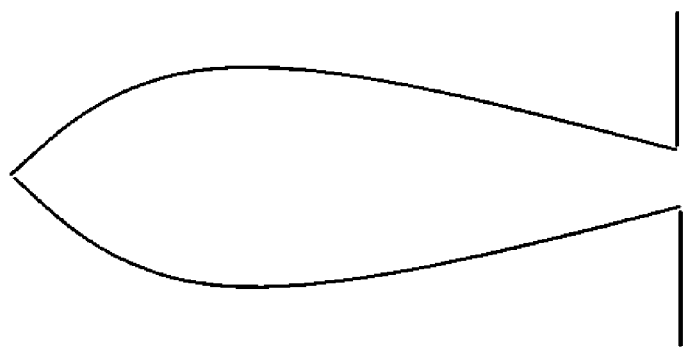
FIG. 5 is a diagram of a microprobe structure according to an embodiment of the present invention.
Figure 6:
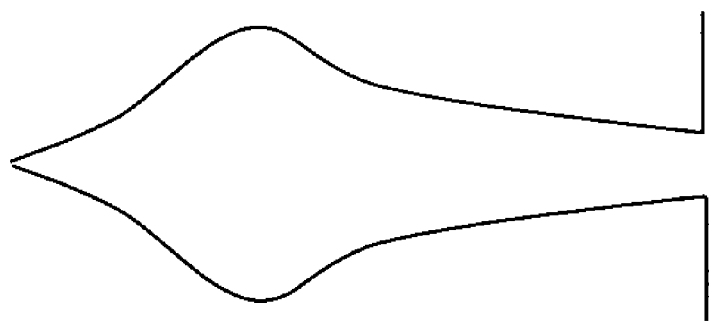
FIG. 6 is a diagram of a microprobe structure according to an embodiment of the present invention.

The bottom of the microprobe comprises that region between the neck 35 to the base 39 of the microprobe. A basis for self stabilization of the microprobe within the skin is based on the neck 35 having greater girth than the base 39 of the microprobe. The contraction of the skin inherently will "push" the microprobe away from the surface of the skin towards the dermis causing greater retention of the microprobe. Accordingly, the shape of the base again need not be a sharp angular shape as seen in FIGS. 3 and 4. but also of a circular or elliptical arc shape which is either concave or convex. In addition, although illustrated in FIGS. 3 and 4 as a sharp angular ridge or edge, the neck 35 of the microprobe can be beveled or circular to cause less potential damage to the cells of the skin, including for example a tear drop shape with the end being pointed, as shown in FIG. 5. In an alternative embodiment, the present invention can further comprise multiple necks 35 to further stabilize the microprobe within the skin. The base of the microprobe can be any suitable shape, including conical, spherical, pyramidal, triangular or any other such suitable shape.

Preferably, the microprobes projecting from carrier penetrate skin so that microprobe tips 34 lie within viable epidermis 50. This provides impedance reducing, electrical signal pathways across stratum corneum 52 without causing pain, discomfort or bleeding of the patient.

Accordingly, the microprobes need to be of a self-stabilizing shape sufficiently sharp and rigid to penetrate the outer layer of the skin of patient while being sufficiently elastic to prevent breaking off when exposed to lateral or bending forces and limiting the depth the microprobe will enter the skin under typical application conditions. At a minimum, the length of the spike should be greater than the depth of the Stratum Corneum 52 (ranging from 10-15 µm with a maximum of about 20 µm, unless wet) but less than the depth of the dermis 54. Preferably, the length of the microprobe ranges from about 20-800 micrometers with a more preferable length of about 20 to about 500 micrometers, most preferably a length to lie within the Stratum Basale or Stratum Germinativum, or the Stratum Spinosum, or via cross-sectional, a length within that region with living conductive cells but less than the dermis. The base 39 of each microprobe should have a radius or width less than that of the neck 35 of the microprobe. Preferably, the range of the base and neck is up to 200 micrometers wide. Microprobes may be sharp to facilitate skin penetration so that tips 34 will be substantially smaller in width than the bases 39.

Typically, the length of the microprobe will determine the depth of the penetration of the microprobe. However, other means for limiting the penetration are also contemplated whether such means are on the microprobe itself or on the substrate. For example, the microprobe can further comprise a long pin and a stop (both not shown) which will limit the depth of penetration of the microprobe. The stop can be similar to the substrate (having a single or multiple microprobes thereon) attached to a pin, such a hierarchal system facilitating microprobe penetration even on patients with hair (which would normally affect penetration depth). The pins would accommodate or account for the hair allowing penetration of the microprobe to a depth no greater than the stop. Such stops can also be on the substrate itself independent of or adjacent to the microprobes, thus limiting the depth of penetration of the microprobes, e.g., a probe having a blunt top.

The dry electrode of the present invention can be formed from a variety of processes and materials known to those skilled in the art. Other sources for materials and processes can be garnered from the semiconductor, MEMS or nanomaterials space, as well as those in biosensors. Microprobes may be manufactured from conductive material such as metal or metal alloys (for example, silver, platinum, steel or the like), electrically conductive plastic or other electroactive poymers (e.g., conductive polysaccharides such as those from bacterial sludge, seaweed or cornstarch), a semiconductor material such as silicon or doped silicon wafers, ceramics including for example oxides, and other such materials known in the art. Alternatively, microprobes could be manufactured from other materials including non-conductive materials, preferably biocompatible, more preferably, biodegradable materials, including such non-conductive materials include polymethyl methacrylate (PMMA) or poly(methyl 2-methylpropenoate), glass, and the like. Preferably, all non-conducting materials, although not limited to non-conductive materials, are coated or doped to make the electrode and/or microprobe more conductive.

Figure 8A:
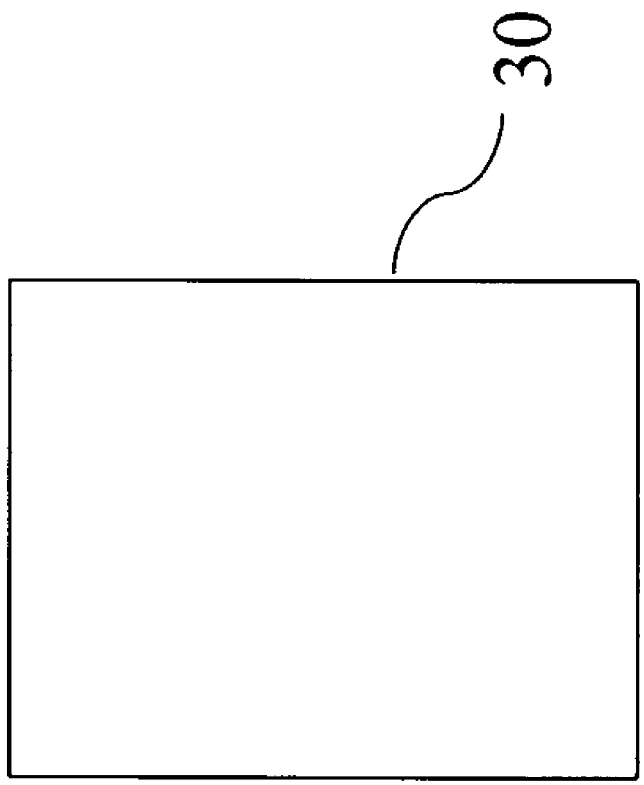
Figure 8B:
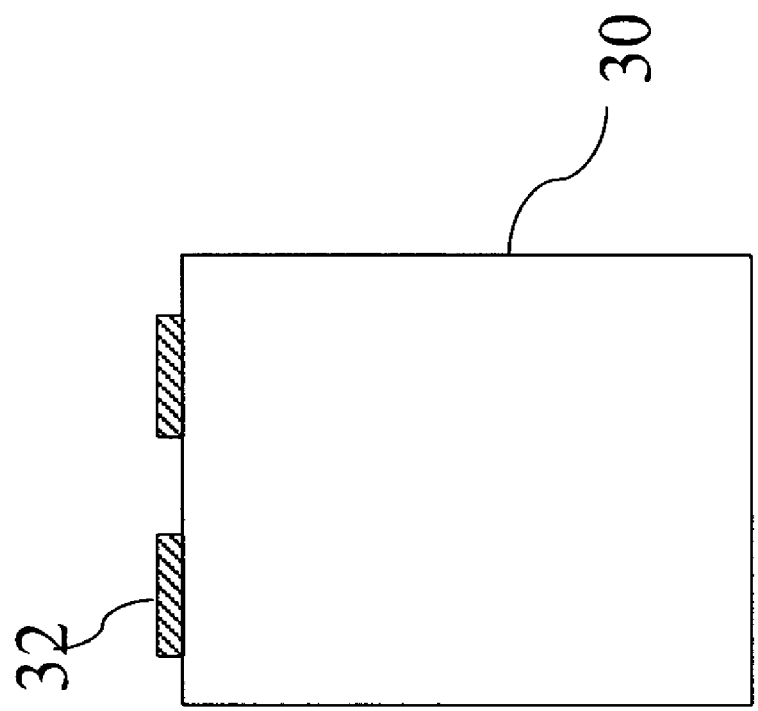
Figure 8D:
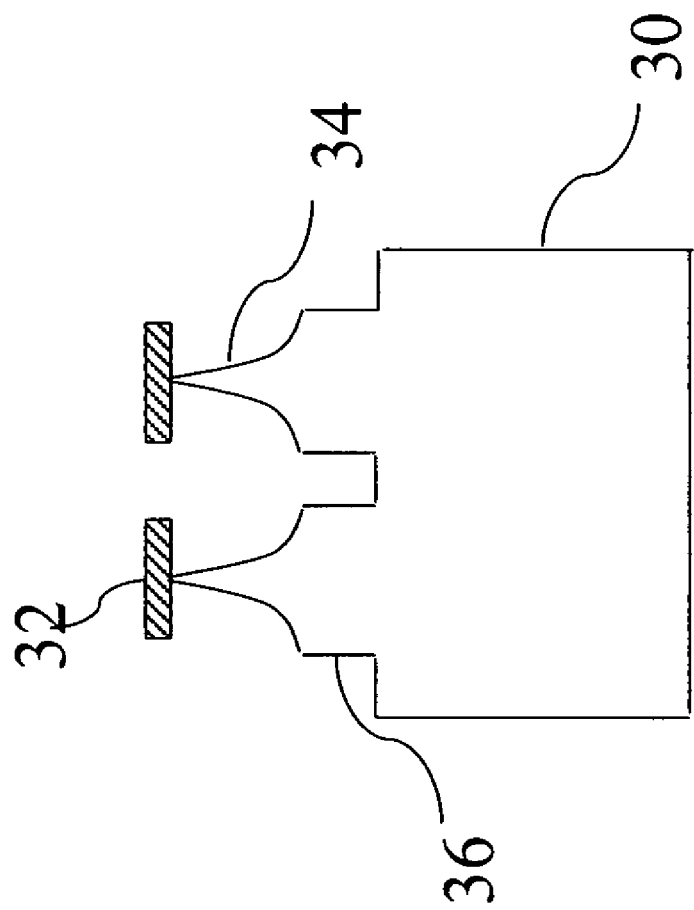
Figure 8F:
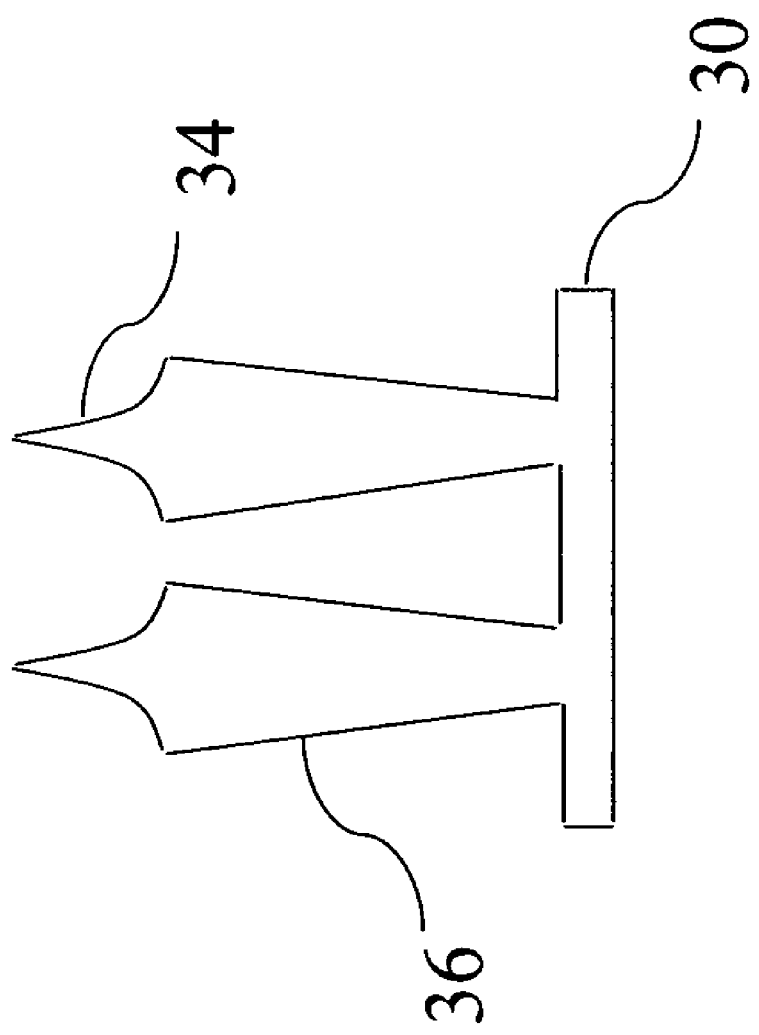
Figure 8G:
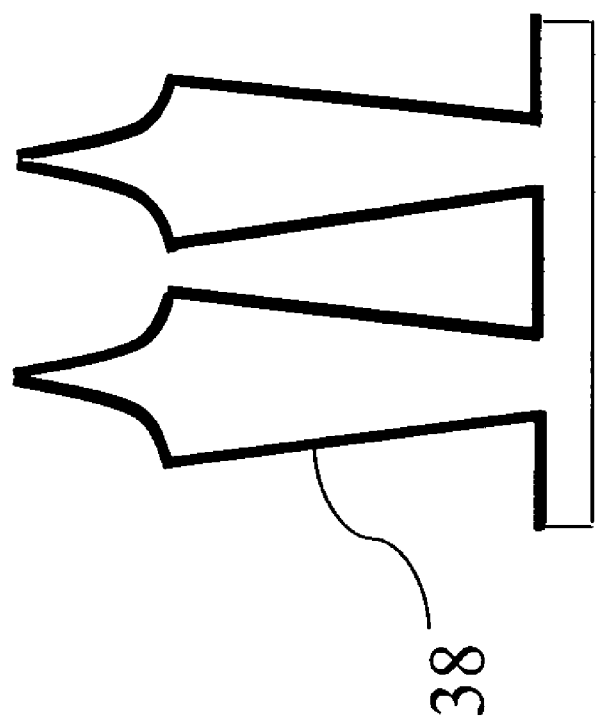

As shown in FIG. 8(G), the surface of the microprobes may also be covered with a suitable material 38, such as a metal, and then coated with a suitable salt. For example, each microprobe can be coated with highly conductive plating such as silver/silver chloride layers, gold, platinum or platinum (platinum/iridium (Pt/Ir), and the like) to improve the signal to noise ratio. The metallization may be applied, after completion of standard MEMs-like knife/needle/spike construction, by vapor deposition, electrolysis, or similar metallic deposition methods. See e.g., Optimum Electrolytic Chloriding of Silver Electrodes, L. A. Geddes, L. E. Baker and A. G. Moore, Med. & Biol. Engineering, Vol. 7, Pergamon Press, 1969; Development of a platinized platinum/iridium electrode for use in vitro, K. Cote and R. Gill, Annals of Biomedical Engineering, Volume 15, Number 5 Springer Netherlands, 1987, 419-426, Electrochemical behaviour of gold, silver, platinum and palladium on the glassy carbon electrode modified by chitosan and its application, Ye X. I, Yang Q., Wang Y. and Li N., Talanta, Volume 47, Number 5, 1998, 1099-1106 (8). Compounds with low electrical resistivity and biomedical compatibility are preferred and known to those of skill in the art. Other conductive layers can also be used or if the microprobes are made of a conducting material, they can be used without deposition of a conducting layer. Alternatively, the microprobes could be fashioned wherein the core of the microprobe leading to the tip is conductive, preferably flexible (e.g., wire), and the self-stabilizing component of the microprobe is nonconductive and, preferably, biocompatible/biodegradable, wherein any breakage will not cause concern of any potential contamination or injury, or the opposite, wherein the core is made of a non-conductive material and dosed with a conductive material on the exterior of the microprobe and/or electrode. In an alternate embodiment of the present invention, the microprobes could be employed to gather spectroscopic bioinformation, for example employing infrared, to determine compositional information. Each microprobe could be employed as an optic fiber to transmit/receive spectroscopic information.

In a further embodiment of the present invention, the medical electrode of the present invention comprises a substrate that includes an array of micro-dimensioned self stabilizing microprobes designed to pierce the outer skin layer, i.e. the stratum corneum and penetrate into the electrically conductive stratum germinativum, thereby to circumvent the high impedance characteristics of the stratum corneum. However, the spikes preferably will not reach the tissue layer below the stratum germinativum containing nerves and blood vessels so as to avoid pain, discomfort, or bleeding or damage to the skin or tissue. Thus, spikes that penetrate the skin more than 10-15 µm, but less than dermis, produce a pain-free electrode-electrolyte interface at the stratum germinativum and transform the ionic current induced by active cells into an electronic current. To achieve this, experiments have shown that the spike length of a majority of the spikes in the array should be in the range of 150 to 350 µm, possibly as long as 500 µm. It may be desirable to vary the length of microprobes within any given array so that measurements are obtained from various depths of the viable epidermis rather than a constant depth. Using varied lengths of microprobes is advantageous because the layers of skin vary in thickness and the skin is invariably not flat, and may also improve self-stabilizing properties of the electrode.

These microprobes are attached to a substrate in an array that allows the electrode to be applied to the surface of the human body to measure a biopotential signal, without causing pain, discomfort or damage to the skin or tissue. The shape of the microprobe array can also be a square, a circle or an irregular shape, such shape generally being dictated by the application. The microprobes can be placed throughout or interspersed on the substrate, e.g., along the edge, in patches, etc. The shape of the microprobe array will be dictated by the application and the shape of the substrate. The substrate can contain from 4-50,000 microprobes, for example in a spaced array wherein the microprobes are spaced 50-500 micrometers apart on the front side or surface of the substrate. However, it is preferable to have a microprobe density of 400 to 2,000 microprobes. The area of a substrate may be from about 2 square millimeters to about several inches, although larger areas as well as smaller areas are also contemplated depending on the application of such electrodes. Generally, the increased efficiency of the electrodes will allow the substrate to be smaller than similar electrodes, wet or dry. In one embodiment, the microprobes are interconnected and they are thus all at the same potential. In another embodiment, the microprobes are grouped to create subarrays of microprobes, e.g., a circuit board with a plurality of traces each leading to a microprobe subarray. In one embodiment, the individual microprobes or array of microprobes are used to detect cardiac depolarization directly, rather than serving as receptors of digital information. ECG tracing can be envisioned by multi-vector sensing of cardiac depolarization by proper placement of the microprobes or array of microprobes and accompanying wiring or conductivity, as opposed to the single vector sensing typically disclosed by other such skin mounted electrodes.

The substrate can be made flexible or rigid or combinations thereof. This can be based on the material of the substrate. The substrate is preferably made from the same material as microprobes, for example as a micromachined silicon chip or substantially different materials, wherein the substrate is made of such materials as fabrics, polymers, plastics, metals, semiconductor material, and the like. Alternatively, the design of the substrate can create the properties of the electrode. For example, the portions of substrate 30 not occupied by electrode areas are formed to possess a desired degree of flexibility so as to allow sensor to form to the contours of the skin of patient on which sensor is placed. A variety of techniques may be used to render these portions of substrate flexible. For example, portions may be sufficiently thin in a direction normal to the surface as to render it flexible. For material having the properties of polycarbonate plastic noted above, the thickness of portions may be less than 0.5 mm, for example, 0.2 to 0.5 mm. Or, the portions of substrate may be perforated with holes to provide the desired amount of flexibility to portion.

An electrical interconnection of the front side and backside of the electrode must be established either directly through substrate or through the exterior of substrate. In one embodiment, a through-hole or holes can be fabricated and both sides substrate coated with a conductive material. By paying special attention that the front side and backside conductive layer coating overlap, the necessary electrical connection may be made between microprobes and lead wire or port. Or, the connection may be obtained by overlapping conductive coatings along the edges of the substrate 30.

An electrical connection between electrode and a bioelectrical monitor or terminal (not shown) may be achieved by a number of various means known in the art, including wireless and wired means. For practical purposes, electrode may be provided with a projecting terminal, e.g., a clip or snap or other similar connector terminal residing on substrate 30, preferably on the side of substrate, as an extension to substrate or on the backside of electrode (i.e., side opposite to microprobes). This allows the electrode to be readily replaceable and disposable, irrespective of whether wired or unwired to the monitor or terminal. Accordingly, leads may connect one or several electrodes to the monitor or terminal using a clip-connector mating to terminal. The information can be transmitted with wires or leads, or alternatively, wireless technologies, including Bluetooth™, ZigBee™, or other proprietary or non-proprietary wireless format, including wireless formats approved for medical use. Those of skill will readily recognize alternative wireless technologies applicable in the present invention to transmit single channel or multi-channel information Electrical leads are attached between the electrode and a monitor or terminal so that the biopotential, or other such information, obtained from the electrode may be analyzed and/or amplified for display or recording. A still further object of the present invention is to provide an electrode which can amplify weak bioelectrical or other such signals. In yet another embodiment of the present invention, an amplifier and battery are attached to the electrode to boost the signal obtained from the subject. The amplifier is not activated until the electrode is in use. This activation may be started by removing a protective tape from the battery and circuitry. A still further object of the present invention is to provide a terminal to analyze and/or display the biosignals. The terminal can be any device which can receive the information and/or display the information, including electronic, graphical, written or printed display such as on PCs, portable devices such as watches, cell-phones and PDAs, print-outs, and other medical and consumer devices typically employed for display, storage and analysis of medical electronic information such as EEG, EKG/ECG, EMG, EOG, and EIT. Other devices and applications will be readily known to those of skill in the art.

Another object of the present invention is to provide such an electrode which may be used without preparing the skin prior to application, and which does not require paste or gels. Although it is contemplated that the electrode will be self secured against the skin once initial pressure is placed on the electrode on the skin, the electrode can be further embodied with means to further stabilize the electrode on the body. The bioelectrode may be kept in position using an adhesive tape or an adhesive on the periphery of the carrier, such as an electrolytic adhesive may be disposed on the underside of the carrier. If desired, the electrode can be used with a conductive gel located between the skin and the carrier, although it may be preferably for the electrode to be used dry. If conductive gel is used (typically held in place with a retainer net or screen material, or such other means known in the art), it may contain antibacterial agents to prevent irritation or infection due to spike penetration of the skin. An electrolytic gel or paste is used in conjunction with an electrode so constructed to make movement artifact less prominent and improve the signal to noise ratio.

Prior to use, microprobes may be protected by a protective paper or film and other suitable means and/or the electrode placed in suitable packaging. The protective paper or film is removed from electrode immediately before the electrode is applied to the patient's skin. Electrode is applied to skin by firmly pressing down on the entire surface of bioelectrode, toward the patient's skin. This pressing action causes microprobes to engage and penetrate skin. The electrical leads are then attached to the electrodes as previously described, and to the bioelectrical monitor that records or displays bioelectrical signals.

The electrode of the present invention can be formed from a variety of processes known to those skilled in the art. These include the general processes typically employed for MEMS or nanomaterial or biosensor devices, including micromachining and semiconductor device manufacturing processes. Current semiconductor processes are now being exploited to develop medical devices and such processes can be readily applied in the current invention process, including deposition, removal, patterning and modification of electrical properties as generally applied in the semiconductor industry. Deposition is any process that grows, coats, or otherwise transfers a material onto the wafer. Available technologies consist of physical vapor deposition (PVD), chemical vapor deposition (CVD), electrochemical deposition (ECD) or similar electroplating techniques, molecular beam epitaxy (MBE) and more recently, atomic layer deposition (ALD) among others. Removal processes are any that remove material from the wafer either in bulk or selective form and consist primarily of etch processes, both wet etching and dry etching such as reactive ion etch (RIE) (also, see, e.g., deep reactive ion etching (DRIE) process). Chemical-mechanical planarization (CMP) is also a removal process used between levels. Patterning covers the series of processes that shape or alter the existing shape of the deposited materials and is generally referred to as lithography. For example, in conventional lithography, the wafer is coated with a chemical called a "photoresist." The photoresist is exposed by a "stepper", a machine that focuses, aligns, and moves the mask, exposing select portions of the wafer to short wavelength light. The unexposed regions are washed away by a developer solution. After etching or other processing, the remaining photoresist is removed by plasma ashing. Modification of electrical properties has historically consisted of doping transistor sources and drains originally by diffusion furnaces and later by ion implantation. These doping processes are followed by furnace anneal or in advanced devices, by rapid thermal anneal (RTA) which serve to activate the implanted dopants. Modification of electrical properties now also extends to reduction of dielectric constant in low-k insulating materials via exposure to ultraviolet light in UV processing (UVP). Different processing steps are also well known to those in the art including front and back end processing and growth of gate dielectrics, Plasma ashing, thermal treatments such as rapid thermal anneal, furnace anneals and oxidation, wafer/device/IC testing, die preparation, packaging steps and other similar steps.

The fabrication of needles extending from the plane of a silicon wafer has been reported in the technical literature. See for example Micromachined Needles for the Transdermal Delivery of Drugs, S. Henry, D. V. McAllister, M. G Allen, and M. R. Prausnitz, Proceedings IEEE Micro Electro Mechanical Systems, 1998; Novel AFM Probes-Fabrication and Characterization, Anja Boisen, Ole Hansen and Siebe Bowastra, Micro Structure Workshop, 1998; and Micromachined, Silicon Based Electrode Arrays for Electrical Stimulation of or Recording from Cerebral Cortex, Richard A. Norman, Patrick K. Campbell and Kelly E. Jones, Proceedings IEEE Micro Electro Mechanical Systems, 1991.

FIGS. 8(a) to 8(k) show one preferred embodiment of the manufacturing steps of the above microprobe array. As shown in FIG. 8(a), a silicon substrate 30 is first provided. A patterned masking layer 32 made of photoresist or thin film material is then defined out on the silicon substrate 30 by means of photolithography, as shown in FIG. 8(b). Next, as shown in FIG. 8(c), a plurality of conical tip portions is isotropically etched with said masking layer as the mask. As shown in FIGS. 8(d) and 8(e), a plurality of needles is anisotropically etched downwards, and etching parameters are controlled to let the ratio of the cross-sectional areas of the connection between the tip portion 34 and the needle 36 and the other end of the needle 36 be larger than 1. Moreover, the connection between the tip portion 34 and the needle 36 has edges and corners or other shapes capable of enhancing the friction between the microprobe and the skin to enhance the stabilization capability of the microprobe. The isotropic and anisotropic etching can be dry etching or wet etching. Subsequently, after the masking layer 32 is removed by means of dry etching or wet etching to get the microprobe structure shown in FIG. 8(f), a conducting layer 38 is formed on the microprobe structure to enhance the electric conductivity of the microprobe for sensing physiologic signals, as shown in FIG. 8(g). The material of the conducting layer 38 is selected among polymer, thin film material and metal. The microprobe array is thus formed.

Because the conducting layers 38 of the microprobes are connected together, this microprobe array can only be used to measure one kind of biopotential signal. Alternatively, various film layers, specific coatings and leads can be coated or deposited onto the electrode to make it individually addressable or to function as desired in an (sub)array. Or the electrode can be doped to increase the conductivity of the electrode.

Figure 8H:
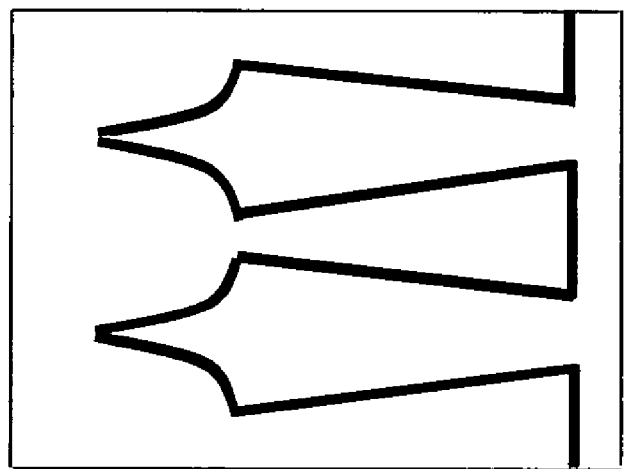
Figure 8I:
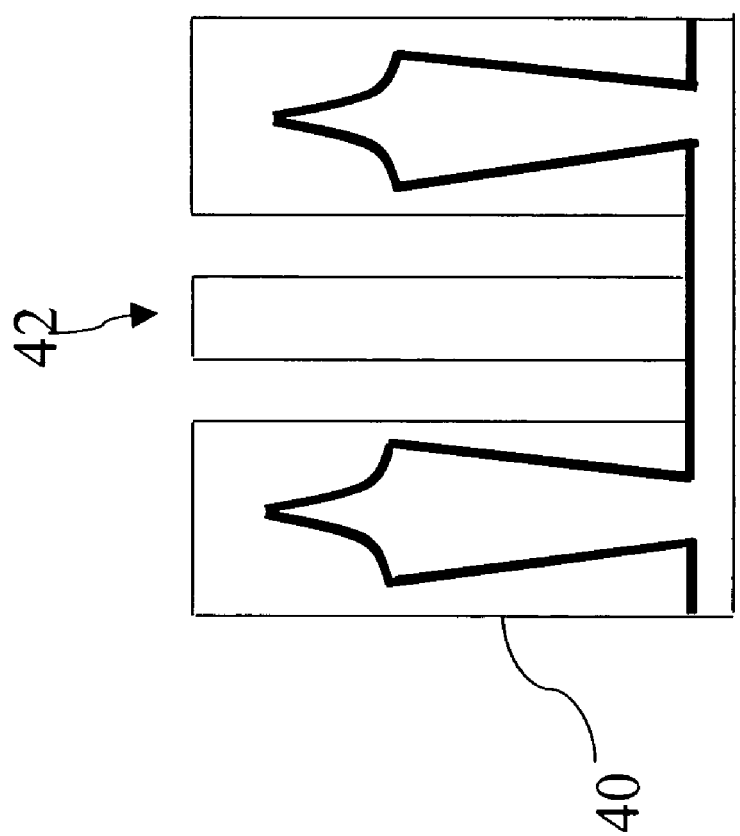
Figure 8J:
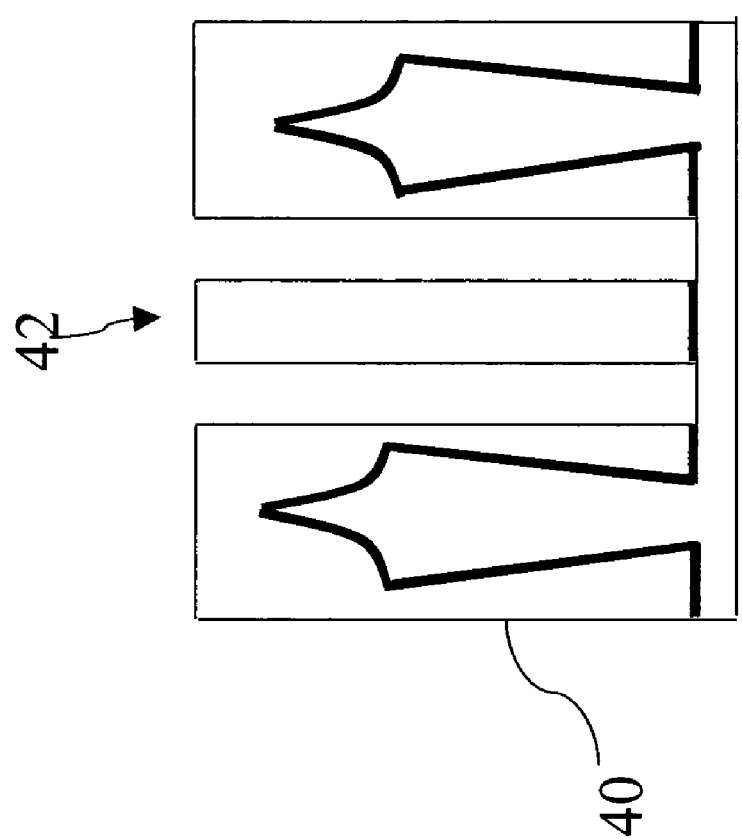
Figure 8K:
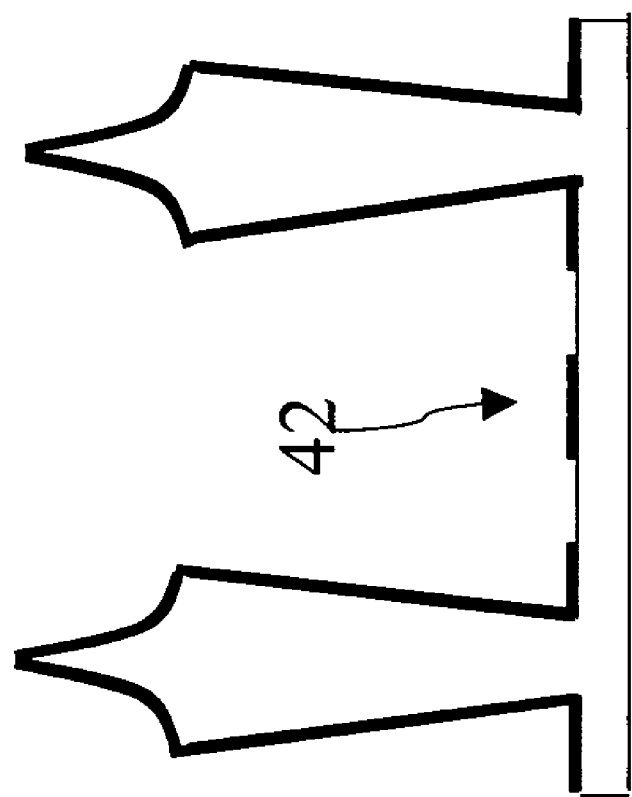

In order to expand the function of the microprobe array, one preferred embodiment of the present invention further proposes a novel design in which part of the conducting layer 39 on the substrate is removed to electrically isolate the microprobes. After the step of FIG. 8(g), a photoresist layer 40 is formed on the plurality of microprobes, as shown in FIG. 8(h). A mask is then formed and a routing 42 is defined out by means of exposure, as shown in FIG. 8(i). Next, the conducting layer outside the microprobe and the routing 42 is removed, as shown in FIG. 8(j). Finally, the photoresist layer 40 is removed to get the microprobe structure with mutually isolated microprobes, as shown in FIG. 8(k). Because the conducting layers between the microprobes are mutually isolated, each microprobe can be separately connected to a different measuring circuit by pulling out the corresponding routing 42. Therefore, the microprobe array can be used for the measurement of various kinds of biopotential signals, and can also be used as stimuli. The whole microprobe array can be used as sensing ends or stimuli, or part of the microprobe array is used as sensing ends while other part of the microprobe array is used as stimuli. When some microprobes are used as stimuli, voltages or currents will be conducted into the microprobes to electrify them; or the microprobes are not electrified but only puncture the skin to render pressure to the punctured location. Other microprobes used as sensing ends are responsible for sensing the stimulation result.

One alternative process contemplated to form the electrode is to form the invention electrode by an additive deposition process. Preferably, an electroplating process is used. Preferably, the substrate for this process is a flexible polymer, and more preferably an insulating polymer such as a polyimide. With this process a thin layer of metal is applied to the substrate. Then a thick layer of photo resist is applied to the thin layer of metal on the substrate and patterned by photolithography to create the desired features, i.e., arrays of squares, circles, etc. These patterns form the base of the electrodes and the other features of the electrode array. The photo resist is stripped from the substrate. Another layer of photoresist is applied. These patterns further define the microprobe structure which is built up to the desired height and shape by electroplating. Optionally, at this point various film layers and leads can be coated onto the electrode to make it individually addressable or to function to improve the conductivity as desired in an array of electrodes.

Yet another invention process is where the electrode can be formed from metal sheet through photo micro-machining techniques, e.g., photo and/or chemical etching, laser machining, abrasion and other metal working techniques are applied on a thin gauge stock of metal to produce the microprobes and the electrode. An array can be better formed by stacking and laminating.

Figure 9C:
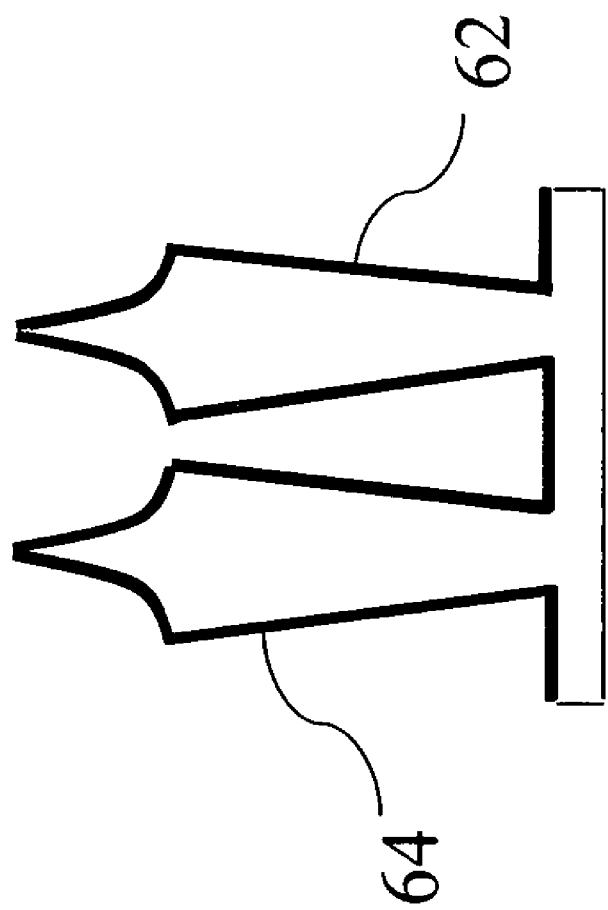

Yet another invention process is to create the electrode by injection molding, casting or depositing a material into a mold. As shown in FIG. 9(a), a mold 60 with the imprint or negative image of the desired surface features which may include the microprobes and substrates, as well as any additional features is formed. In FIG. 9(b), this mold 60 may be filled via injection molding, casting, deposition or other material forming technique to produce the desired electrode 62. Optionally and as a function of the conductivity of the material utilized, as shown in FIG. 9(c), the surface may be doped to increase the conductivity of the electrode, and also various film layers and leads can be coated onto the electrode 62 to make it individually addressable or to function as desired in an array of electrodes.

Those of skill in the art will readily recognize additional processes which can be applied in forming invention electrodes. In addition to functionality of the electrode, those of skill in the art will readily recognize that other attributes, such as cost, availability of electrode materials and fabrication materials, ease of manufacture, regional and regulatory concerns, biocompatibility, acceptance by industry, and other such factors will dictate the fabrication of the invention electrode.

The electrodes of the present invention can be used in a variety of applications including but not limited to ECG, EEG, EIT, EMG, and EOG. The electrodes can be packaged by conventional packaging techniques, however, preferably the package provides 1) adequate structural support for the electrode so it can be handled roughly (i.e., dropped, crushed, etc) without damage; 2) a means (i.e., a spring, etc) to force the electrode against the subjects skin with a consistent pressure; 3) a low impedance path from the electrodes surface to the package's output connector; 4) a design which allows for easy cleaning and sterilization for applications requiring reuse; 5) a design to allow disposability of electrode and/or packaging; 6) a design to easily activate or expose electrode; and 7) a design to allow the user to readily determine prior use and/or other such safety and cross-contamination concerns, including infection.

The dry physiological recording electrodes are applied to an animal or human body having skin comprising an epidermis comprising a stratum corneum layer and lower layers of the epidermis, and a dermis. The microprobes(s) of the electrode pierce through the stratum corneum layer of the skin with the microprobe(s) such that the microprobe(s) does not enter the dermis of the skin. When attached to the skin of the subject, microprobe(s) obtains biopotential signals or provides electrostimulation of body tissue. The microprobe(s) senses the ionic current in the lower layers of the epidermis, and transforms a portion of the ionic current of the lower layers of the epidermis of the skin into an electric voltage through the microprobe(s). The electric voltage from the microprobe(s) is measured using conventional measuring devices.

The electrode of the present invention may also be used to enhance the administration of skin applied drugs. To this end, a drug container, such as a flexible capsule, may be provided on the backside of the electrode. A plurality of through-holes may be provided in substrate to discharge the drug to the skin of the subject when the flexible capsule is pressed. The penetration of the skin by the spikes facilitates passage of the drug through the stratum corneum. The length of the microprobes in such an application also should be the same as for electrodes without such feature thus inflicting no pain to the patient. The drug delivery can be combined with electrical stimulation.

To sum up, the present invention provides two microprobe structures (one with electrically connected microprobes and the other with electrically isolated microprobes) and their manufacturing methods. Moreover, the microprobes of these two structures have the self-stabilization capability in the skin tissue. Because the substrate of the microprobe array of the present invention is silicon, a very high supporting force in the longitudinal direction can be provided, and the shrinkage of the bottom of the needle 36 has little influence to the longitudinally exerted force of the structure. Besides, because the Stratum Corneum 50 and the Stratum Germinativum 52 of the skin will come off themselves due to metabolism, it is not necessary to worry about that the probe may be remained in the skin. The length of the microprobe array (i.e., the total length of the tip portion 34 and the needle 36, about 240~450 micrometers) is designed in accordance with the human race or age range to be measured, it won't get into the dermis 54 to cause pain or bleeding to the measured person.

Although the present invention has been described with reference to the preferred embodiments thereof, it will be understood that the invention is not limited to the details thereof Various substitutions and modifications have been suggested in the foregoing description, and other will occur to those of ordinary skill in the art. Therefore, all such substitutions and modifications are intended to be embraced within the scope of the invention as defined in the appended claims.

What is claimed is:

1. A microprobe structure used to measure biopotential signals, said microprobe structure comprising:
   an elongated tapering needle member having an increasing width in a first section integrally formed with a second section, said second section having an acute contour terminating at a point to define a tip portion; and
   a conducting layer covering said needle member including said tip portion.

2. The microprobe structure as claimed in claim 1, wherein said tip portion is conical.

3. The microprobe structure as claimed in claim 1, wherein said tip portion can puncture the Stratum Corneum and Stratum Germinativum to allow said microprobe to get into said Stratum Germinativum and measure said biopotential signals.

4. The microprobe structure as claimed in claim 1, wherein said biopotential signals include electroencephalographic (EEG) signals, electrocardiographic (ECG) signals and electromyographic (EMG) signals.

5. The microprobe structure as claimed in claim 1, wherein the total length of said tip portion and said needle member is 250~450 micrometers.

6. The microprobe structure as claimed in claim 1, wherein a connection between said tip portion and a remaining portion of said needle member includes edges and corners to enhance a stabilization capability of said microprobe.

7. The microprobe structure as claimed in claim 1, wherein a ratio of a cross-sectional area at an interface between said tip portion and a remaining portion of said needle member and a bottom of said needle member is larger than 1.

8. The microprobe structure as claimed in claim 1, wherein the material of said conducting layer is polymer, thin film material or metal.

9. The microprobe structure as claimed in claim 1, wherein a bottom of said needle member is connected to a substrate and used as a sensing electrode that is connected to an external circuit and used to receive said measured biopotential signals.

10. The microprobe structure as claimed in claim 9, wherein the material of said substrate is silicon.

11. The microprobe structure as claimed in claim 9, wherein a plurality of said microprobes is disposed on said substrate to form a microprobe array.

12. The microprobe structure as claimed in claim 11, wherein said conducting layers of said microprobes are connected together to measure one of said biopotential signals.

13. The microprobe structure as claimed in claim 11, wherein said conducting layers of said microprobes are mutually isolated, and said microprobe array is used to measure a plurality of said biopotential signals.

14. The microprobe structure as claimed in claim 13, wherein each of said microprobes with mutually isolated conducting layers is used as a stimulus.

15. The microprobe structure as claimed in claim 14, wherein when said microprobe is used as a stimulus, a voltage or a current is conducted into said microprobe to electrify said microprobe or render pressure to the punctured location.

16. The microprobe structure as claimed in claim 11, wherein the shape of said microprobe array is a square, a circle, or an irregular shape.

17. The microprobe structure as claimed in claim 1, wherein the needle member including the tip portion is hollow.

18. A microprobe array structure used to measure biopotential signals, said microprobe array structure comprising:
a substrate; and
a plurality of microprobes each having an elongated tapering needle member having an increasing width in a first section integrally formed with a second section, said second section having an acute contour terminating at a point to define a tip portion, and a bottom of said needle member being connected to said substrate, wherein a conducting layer coats said needle member including said tip portion.

19. The microprobe array structure as claimed in claim 18, wherein said tip portion is conical.

20. The microprobe array structure as claimed in claim 18, wherein said tip portion can puncture the Stratum Corneum and Stratum Germinativum to allow said microprobe to get into said Stratum Germinativum and measure said biopotential signals.

21. The microprobe array structure as claimed in claim 18, wherein said biopotential signals include electroencephalographic (EEG) signals, electrocardiographic (ECG) signals and electromyographic (EMG) signals.

22. The microprobe array structure as claimed in claim 18, wherein the total length of said needle member including said tip portion is 250~450 micrometers.

23. The microprobe array structure as claimed in claim 18, wherein a connection between said tip portion and a remaining portion of said needle member includes edges and corners to enhance a stabilization capability of said microprobe.

24. The microprobe array structure as claimed in claim 18, wherein a ratio of a cross-sectional area at an interface between said tip portion and a remaining portion of said needle member and a bottom of said needle member is larger than 1.

25. The microprobe array structure as claimed in claim 18, wherein the material of said conducting layer is polymer, thin film material or metal.

26. The microprobe array structure as claimed in claim 18, wherein said substrate is used as a sensing electrode that is connected to an external circuit and used to receive said measured biopotential signals.

27. The microprobe array structure as claimed in claim 18, wherein the material of said substrate is silicon.

28. The microprobe array structure as claimed in claim 18, wherein said conducting layers of said plurality of microprobes are connected together to measure one of said biopotential signals.

29. The microprobe array structure as claimed in claim 18, wherein said conducting layers of said plurality of microprobes are mutually isolated, and said microprobe array is used to measure a plurality of said biopotential signals.

30. The microprobe array structure as claimed in claim 29, wherein each of said microprobes with mutually isolated conducting layers is used as a stimulus.

31. The microprobe array structure as claimed in claim 30, wherein when said microprobe is used as a stimulus, a voltage or a current is conducted into said microprobe to electrify said microprobe or render pressure to the punctured location.

32. The microprobe array structure as claimed in claim 18, wherein a shape of each of said plurality of microprobes is a square, a circle, or an irregular shape.

33. The microprobe array structure as claimed in claim 18, wherein the microprobe is hollow.

* * * * *